(12) United States Patent
Askar et al.

(10) Patent No.: US 9,017,652 B1
(45) Date of Patent: Apr. 28, 2015

(54) COMBINATION OF CROSSLINKED CATIONIC AND AMPHOLYTIC POLYMERS FOR PERSONAL AND HOUSEHOLD APPLICATIONS

(75) Inventors: Narjis A. Askar, Bartlett, IL (US); Yin Z. Hessefort, Naperville, IL (US); Cheryl A. Slabozeski, Crest Hill, IL (US); Jobiah J. Sabelko, Sugar Grove, IL (US); Yasuhiro Doi, Wakayama (JP)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 396 days.

(21) Appl. No.: 12/757,720

(22) Filed: Apr. 9, 2010

(51) Int. Cl.
*A61K 8/02* (2006.01)
*A61K 8/36* (2006.01)
*A61K 8/37* (2006.01)
*A61K 8/42* (2006.01)
*A61K 8/46* (2006.01)
*A61K 8/81* (2006.01)

(52) U.S. Cl.
CPC .................................. *A61K 8/8158* (2013.01)

(58) Field of Classification Search
CPC ........ C08F 220/06; C08F 220/56; A61K 8/81
USPC .......... 510/119, 127, 130; 525/55; 424/70.16, 424/70.17, 70.21, 70.22, 70.27, 70.31
See application file for complete search history.

(56) References Cited

U.S. PATENT DOCUMENTS

| | | |
|---|---|---|
| 5,417,965 A | 5/1995 | Janchitraponvej et al. |
| 5,573,709 A | 11/1996 | Wells |
| 6,069,216 A | 5/2000 | Iwasaki et al. |
| 6,110,451 A * | 8/2000 | Matz et al. ................. 424/70.16 |
| 6,180,576 B1 * | 1/2001 | Melby et al. .................. 510/121 |
| 6,183,732 B1 | 2/2001 | Salmon |
| 7,115,254 B1 * | 10/2006 | Brandt et al. .............. 424/70.11 |
| 7,951,762 B2 * | 5/2011 | Doi et al. ...................... 510/119 |
| 7,960,327 B2 * | 6/2011 | Uchiyama et al. ............ 510/130 |
| 7,981,850 B2 * | 7/2011 | Doi et al. ...................... 510/119 |
| 2003/0165454 A1 * | 9/2003 | Snyder et al. .............. 424/70.16 |
| 2004/0151685 A1 * | 8/2004 | Popescu et al. ............ 424/70.14 |
| 2007/0207106 A1 * | 9/2007 | Sabelko et al. .............. 424/70.7 |

FOREIGN PATENT DOCUMENTS

| | | |
|---|---|---|
| EP | 1466592 A1 | 10/2004 |
| FR | 2920982 A1 | 3/2009 |
| JP | 2009-173586 A | 8/2009 |
| WO | 00/37041 A1 | 6/2000 |
| WO | 01/76543 A1 | 10/2001 |
| WO | 03/074020 A1 | 9/2003 |
| WO | WO2007/077668 * | 7/2007 |
| WO | WO 2008/081591 A1 * | 7/2008 |

OTHER PUBLICATIONS

SciFinder Scholar data on Polyquaternium 39 (Retrieved on Dec. 27, 2011).*
SciFinder Scholar data on Polyquaternium 37 (Retrieved on Dec. 27, 2011).*
SciFinder Scholar data on Polyquaternium 52 (Retrieved on Dec. 28, 2011).*
Lubrizol (Technical Data Sheet Merquat TM 2003PR Polymer Data, Retrieved Dec. 28, 2011, http://www.lubrizol.com/PersonalCare/Products/Merquat2003PR.html).*
Nalco Personal Care Products Index (http://mascot.in/pdf/Nalco_Personal_Care_Products_Index.pdf, Retrieved Dec. 28, 2011).*
Conditioning Polymers Provide Multiple Benefits, retrieved from www.personalcaremagazine.com, XP-002662657, Mar. 2011, pp. 1-3.

* cited by examiner

Primary Examiner — Richard Schnizer
Assistant Examiner — Alma Pipic
(74) Attorney, Agent, or Firm — Christopher P. Demas

(57) ABSTRACT

A cleansing composition for cosmetic or household use may include an ampholytic polymer; a crosslinked cationic polymer; a surfactant component selected from the group consisting of anionic surfactants, amphoteric surfactants, cationic surfactants, nonionic surfactants, and zwitterionic surfactants; and an aqueous and/or organic carrier.

5 Claims, No Drawings

COMBINATION OF CROSSLINKED CATIONIC AND AMPHOLYTIC POLYMERS FOR PERSONAL AND HOUSEHOLD APPLICATIONS

BACKGROUND OF INVENTION

1. Field of the Invention

Embodiments disclosed herein relate generally to compositions containing a crosslinked cationic polymer and an ampholytic polymer and methods of using the composition for consumer and/or industrial applications.

2. Background Art

Cationic polymers have been used widely in personal care, household, industrial, and institutional products to perform a function in the final product, ranging from the use of the polymer as gellants, binders, thickeners, stabilizers, emulsifiers, spreading and deposition aids, and carriers for enhancing the rheology, efficacy, deposition, aesthetic and delivery of chemically and physiologically active ingredients in personal care, (e.g., cosmetic, oral care, baby care), household, or pet care compositions. Depending on the application, the substrate may be skin, hair, or textile substrates, etc.

Cationic polymers are used in hair care products to provide conditioning to the hair. In skin care products, these same polymers can provide conditioning effects to the skin. When incorporated into detergent and fabric softening formulations, these same polymers can provide conditioning, softening, anti-pilling, color retention, and antistatic characteristics to fabrics.

Hair is composed of keratin, a sulfur-containing fibrous protein. The isoelectric point of keratin, and more specifically of hair, is generally in the pH range of 3.2-4.0. Therefore, at the pH of a typical shampoo (about 5.5-6.5), hair carries a net negative charge. Consequently, cationic polymers due to their positive charge have long been used as conditioners in shampoo formulations, or as a separate treatment, in order to improve the wet and dry combability of the hair. The substantivity of the cationic polymers for negatively charged hair along with film formation facilitates detangling during wet hair combing and a reduction in static flyaway during dry hair combing. Cationic polymers generally also impart softness and suppleness to hair. Thus, while most shampoos incorporate conditioners into the shampoo to help alleviate these problems, this brings the inherent problem of balancing cleansing efficiency against delivering a conditioning benefit. For example, when cationic polymers are added to shampoos containing anionic surfactants, formation of highly surface active association complexes generally takes place, which imparts improved foam stability to the shampoo but may provide poor conditioning. Maximum surface activity or lather, are achieved at near stoichiometric ratios of anionic surfactant: cationic polymer, where the complex is least water soluble. However, cationic conditioners often exhibit some incompatibility at these ratios. Compatibility gives a commercially more desirable clear formulation, while incompatibility leads to a haze or precipitation, which is aesthetically less desirable in some formulations. Additionally when cationic surfactants are added as an ingredient in the shampoo, they do not provide optimal overall conditioning to the hair in the area of softness and tend to build up on the hair resulting in an unclean feel.

The minimum function of a shampoo is to cleanse the hair. Cleansing is accomplished by removal of natural oils called sebum, and extraneous substances, which accumulate from the atmosphere or are added intentionally, like styling resins. However, shampooing removes natural oils and other moisturizing materials. In order to be acceptable to consumers, a product must exhibit good cleansing properties, good lathering characteristics, must be mild to the skin and preferably moisturize the skin. Ideal shampoos should gently cleanse the hair and scalp and cause little or no irritation, and not leave the scalp or hair overly dry after frequent use. Traditional shampoos have the inherent problem of balancing cleansing efficacy against delivering a conditioning benefit. If the hair is of significant length, the hair can be tangled and becomes unmanageable. Once dry, the hair has lost its shine and luster and can be dry and frizzy. Hair can also maintain a static charge when dry that results in "fly-away hair." If a shower is taken at the time of this shampooing, the natural oils etc. are also removed from the skin and nails.

The use of known high sudsing anionic surfactants with foam boosters yields acceptable lather volume but they are known to give skin irritation. Mild surfactants, which give minimal skin irritation are extremely poor in lather. These two facts alone make the selection of surfactants for optimization of lather performance a delicate balancing act. Mildness is often obtained at the expense of effective cleansing and lathering. If a conditioning ingredient in a shampoo system can help generate a good quality foam most of the problems mentioned above can be reduced drastically.

Further complicating this balance is the desire to further modify a shampoo to minimize color fading on dyed hair. Hair color technology has significantly evolved over the years making the hair colors more fade resistant to cater to the high expectations of consumers who want the colors to last for many shampoos. Color fading is associated with the hair looking dull and having less shine. There is a growing demand for products that protect hair color.

Even for non-dyed hair, through daily washing and styling regimens, hair can be stripped of its moisture and natural oils, becoming brittle and dull. Hair that has been temporarily or permanently dyed is thus especially in need of protection to maintain its condition and color. Due to their small size the dye molecules easily leach out of the hair, leading to fading or a change in tone upon exposure to environmental, physical, mechanical or chemical damage. Keeping in view the cost and long-term damage of hair dyeing, it is desirable to minimize the loss of color. Furthermore for hair that has been subjected to two chemical treatments or which is subjected to heated styling regimens everyday, leaves the hair harder to manage and color to fade, requiring special products and ingredients that cater to this need.

Silicones and film forming polymers, as well as olefin graft polymers, have been used to protect the hair color from fading. The incorporation of these components can further shift the delicacy of shampoo formulations. For example, when various silicones are added to shampoos containing good cleaning anionic surfactants, while improved conditioning properties and color retention properties may be observed, the silicones tend to build up on the hair after repeated shampoo application causing the hair to take on a greasy, unclean appearance.

As mentioned above, the use of these cationic conditioning polymers is not limited to the hair, but is often used in other personal care, (e.g., cosmetic, oral care, baby care), pet care, or household compositions. When consumers launder fabrics, they desire not only excellence in cleaning, they also seek to impart superior fabric care benefits. Such care may be exemplified by one or more of reduction, removal, or prevent of wrinkles benefits, fabric softness, fabric feel, garment shape retention and recovery, elasticity, ease of ironing, perfume, color care, anti-abrasion, anti-pilling, or any combination thereof. Compositions which provide both cleaning and fabric care benefits, e.g., fabric softening benefits, are known as "2 in 1" detergent compositions and/or as "softening-through-the-wash"-compositions.

Accordingly, there exists a continuing need for the combination of polymers that may be effective in a broad class of application, but may be particularly suitable for use in providing enhanced foam quality and in color protection in personal and household applications.

SUMMARY OF INVENTION

In one aspect, embodiments disclosed herein relate to a cleansing composition for cosmetic or household use that includes an ampholytic polymer; a crosslinked cationic polymer; a surfactant component selected from the group consisting of anionic surfactants, amphoteric surfactants, cationic surfactants, nonionic surfactants, and zwitterionic surfactants; and an aqueous and/or organic carrier.

In another aspect, embodiments disclosed herein relate to a method of treating a household surface comprising applying the composition that includes an ampholytic polymer; a crosslinked cationic polymer; a surfactant component selected from the group consisting of anionic surfactants, amphoteric surfactants, cationic surfactants, nonionic surfactants, and zwitterionic surfactants; and an aqueous and/or organic carrier to a household surface, an industrial surface, a hard surface, a carpet, a fabric, wood, vinyl or a plastic containing composition.

In another aspect, embodiments disclosed herein relate to a method of treating a surface comprising applying the composition that includes an ampholytic polymer; a crosslinked cationic polymer; a surfactant component selected from the group consisting of anionic surfactants, amphoteric surfactants, cationic surfactants, nonionic surfactants, and zwitterionic surfactants; and an aqueous and/or organic carrier to hair, skin, nails, or a keratin containing substrate.

In yet another aspect, embodiments disclosed herein relate to a method for treating keratin substrate comprising contacting hair with the composition that includes an ampholytic polymer; a crosslinked cationic polymer; a surfactant component selected from the group consisting of anionic surfactants, amphoteric surfactants, cationic surfactants, nonionic surfactants, and zwitterionic surfactants; and an aqueous and/or organic carrier, wherein said ampholytic polymer is selected from a group of polymers consisting (1) a polymer comprised of about 40 mol % of MAPTAC, about 50 mol % of acrylamide and 10 mol % of acrylic acid and (2) a polymer comprised of about 45 mol % MAPTAC, about 45 mol % acrylic acid, and about 10 mol % methylacrylate, and (3) a polymer comprised of about 30 mol % DADMAC, about 35 mol % acrylic acid, and about 35 mol % acrylamide, and (4) a polymer comprised of about 64 mol % DADMAC, about 36 mol % acrylic acid, and wherein said crosslinked cationic polymer consists of about 1 to 99 wt % N,N-dimethlyaminoethyl methacrylate diethyl sulfate quaternary salt, about 1 to 99 wt % N,N-dimethylacrylamide, and about 0.002-5 wt % polyethylene glycol dimethacrylate polymer.

In yet another aspect, embodiments disclosed herein relate to a method for treating keratin substrate comprising contacting hair with the composition that includes that includes an ampholytic polymer; a crosslinked cationic polymer; a surfactant component selected from the group consisting of anionic surfactants, amphoteric surfactants, cationic surfactants, nonionic surfactants, and zwitterionic surfactants; and an aqueous and/or organic carrier, wherein said ampholytic polymer comprises about 40 mol % of MAPTAC, about 50 mol % of acrylamide and 10 mol % of acrylic acid, and wherein said crosslinked cationic polymer comprises about 10 mol % N,N-dimethylaminoethyl methacrylate diethyl sulfate quaternary salt, about 90 mol %, N,N-dimethylacrylamide, about 0.002-5 wt % polyethylene glycol dimethacrylate copolymer.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

DETAILED DESCRIPTION

In one aspect, embodiments disclosed herein relate to compositions containing a combination of a cationic polymer and an ampholytic polymer and methods of using the composition for consumer and/or industrial applications. Specifically, embodiments of the present disclosure provide for a composition containing a crosslinked, cationic polymer, an ampholytic polymer, and at least one surfactant. The compositions may provide excellent foam quality, as well as color retention, for use in a wide variety of personal, household, and industrial products.

It has now been unexpectedly found that improved foam and color retention properties may be synergistically achieved by combining the ampholytic polymer and crosslinked cationic polymer of the present disclosure while still maintaining excellent conditioning properties. These compositions may provide improved conditioning, lather, and color protection while reducing the level of undesirable side effects that can result from increasing the level of conditioning agent in prior known conditioning systems. Specifically, the inventors of the present disclosure have found that the combination of these components provides a synergistic effect for foam quality and color retention, whereby the improvement in properties achieved when the two components are used together is significantly improved over use of the two independently.

Ampholytic Polymer

The ampholytic polymer of the present disclosure may include, as its constituent monomers, (1) an anionic monomer, (2) a cationic monomer, and (3) an optional non-ionic monomer. Exemplary anionic monomers may include, as representative anionic monomers, acrylic acid, methacrylic acid, itaconic acid, 2-acrylamido-2-methyl-1-propanesulfonic acid, sulfopropyl acrylate or methacrylate or other water-soluble forms of these or other polymerizable carboxylic or sulfonic acids, sulphomethylated acrylamide, allyl sulphonate, styrene sulfonic acid, sodium vinyl sulphonate, and the like. Further, one of ordinary skill in the art will appreciate that these monomers may be incorporated as the base addition salt thereof, which is the salt resulting from reaction of a carboxylic acid ($-CO_2H$) group with a suitable base such as the hydroxide, carbonate, or bicarbonate of a metal cation or tetraalkylammonium cation, or with ammonia, or an organic primary, secondary, or tertiary amine of sufficient basicity to form a salt with the carboxylic acid group. Representative alkali or alkaline earth metal salts include sodium, lithium, potassium, calcium, magnesium, and the like. Representative organic amines useful for the formation of base addition salts include ethylamine, diethylamine, ethylenediamine, ethanolamine, diethanolamine, piperazine, and the like. Preferred base addition salts include the sodium and ammonium salts. Further, it should also be understood that the anionic monomer refers to a monomer containing an acid group capable of being deprotonated, and a monomer may not necessarily be present in the deprotonated form, but that a monomer containing a degree of unsaturation and a group capable of being deprotonated (whether or not actually deprotonated) is within the scope of the present disclosure.

Exemplary cationic monomers may include, for example, acid-neutralized compounds or quaternary ammonium salts of amino group-containing monomers including dialkylamino group-containing (meth)acrylic esters or (meth)acrylamides such as dimethylaminoethyl (meth)acrylate, diethylaminoethyl (meth)acrylate, dipropylaminoethyl (meth)acrylate, diisopropylaminoethyl (meth)acrylate, dibutylaminoethyl (meth)acrylate, diisobutylaminoethyl (meth)acrylate, di-t-butylaminoethyl (meth)acrylate, dimethylaminopropyl (meth)acrylamide, diethylaminopropyl (meth)acrylamide, dipropylaminopropyl (meth)acrylamide, diisopropylaminopropyl (meth)acrylamide, dibutylaminopropyl (meth)acrylamide, diisobutylaminopropyl (meth)acrylamide, and di-t-butylaminopropyl (meth)acrylamide, and diallyl-having quaternary ammonium salts such as dimethyldiallyl ammonium chloride and diethyl diallyl ammonium chloride.

In a particular embodiment, the cationic monomers may include acid-neutralized compounds or quaternary ammonium salts of dialkyl aminoalkyl acrylamides, dialkyl aminoalkyl methacrylamides, dialkyl aminoalkyl acrylates or dialkyl aminoalkyl methacrylates. In another embodiment, the cationic monomers may be selected from compounds having the following formula (I):

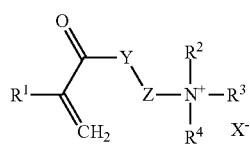

wherein $R^1$ is a hydrogen atom or methyl group, $R^2$ and $R^3$ are identical to or different from each other and represent an alkyl or alkenyl group of 1 to 4 carbons, $R^4$ represents a hydrogen atom or alkyl group of 1 to 4 carbons, Y represents an O, NH, or O—CH$_2$CH(OH) group, Z represents a linear or branched alkyl and or alkylene group of 1 to 6 carbons, and X represents a conjugate base of the acid, halogen atom, or alkyl sulfate group of 1 to 4 carbons. In a particular embodiment, $R^1$ is a methyl group, Y is a NH, Z is a propyl group, $R^2$ to $R^4$ are all methyl groups, and X is a chlorine.

Exemplary non-ionic monomers may include, for example, non-ionic derivatives of acrylic acid, such as (meth)acrylamide, N-methyl (meth)acrylamide, N,N-dimethyl (meth)acryl amide, N,N-diethyl (meth)acrylamide, N-n-propyl (meth)acrylamide, N-isopropyl (meth)acrylamide, N-t-butyl (meth)acrylamide and N-isobutyl (meth)acrylamide, a $C_1$-$C_{22}$ straight or branched chain alkyl acrylate or methacrylate, a $C_1$-$C_{22}$ straight or branched chain n-alkyl acrylamide or methacrylamide, acrylamide methylacrylamide, n-vinylpyrrolidone, vinyl acetate or ethoxylated and propoxylated acrylate or methacrylate.

The ampholytic polymer of the present disclosure includes at least one cationic monomer, one anionic monomer however, in a particular embodiment, the ampholytic polymer may be an acrylic acid/acrylamide/methylacrylamidopropyl trimethyl ammonium chloride polymer. Further, cationic component may be present in an amount ranging from 1-99 mol % the anionic component in an amount ranging from 1 to 99 mol %, and the nonionic component in an amount ranging from 0 to 99 mol %. In another embodiment, cationic component may be present in an amount ranging from 10 to 60 mol % (or 30 to 50 mol % in a more particular embodiment) the anionic component in an amount ranging from 1 to 40 mol % (or 5 to 25 mol % in a more particular embodiment), and the nonionic component in an amount ranging from 0 to 80 mol % (or 30 to 60 mol % in a more particular embodiment). In yet another embodiment, the cationic component may be present at about 40 mol %, the anionic component at about 10 mol %, most preferably and the nonionic component at about 50 mol %.

The ampholytic polymer of the present disclosure may be prepared by any radical polymerization techniques known in the art, such as, precipitation polymerization in an aqueous medium, suspension polymerization, reverse-phase suspension polymerization, emulsion polymerization, solution polymerization, or by any other suitable methods. The radical formation may be achieved by the use of a radical polymerization catalyst or initiators or by irradiation or exposure to electron or ultraviolet rays. Examples of such radical polymerization catalysts are free-radical initiators such as peroxides (e.g., hydrogen peroxide, benzoyl peroxide and cymene hydroperoxide); azo compounds (e.g., azobisisobutyronitrile and azobiscyanovaleric acid; and persulfates (e.g., ammonium persulfate and potassium persulfate); as well as redox initiators consisting of a combination of the above free-radical initiator and a reducing agent such as sodium hydrogensulfite or L-ascorbic acid. Examples of the polymerization medium include water, aqueous electrolyte solutions, methanol, acetone and dimethylformamide, although the selection of the medium may depend on the polymerization technique employed. With respect to the conditions for polymerization, they are not particularly limited and may conveniently be selected depending on the polymerization technique employed.

The molecular weights of the ampholytic polymers of the present disclosure may broadly range from about 10,000 daltons to 15,000,000 daltons. Further, the compositions of the present disclosure may broadly include at least 0.01 to 10 weight percent of the ampholytic polymer.

Crosslinked, Cationic Polymer

The crosslinked, cationic polymer of the present disclosure may include, as its constituent monomers, (1) a cationic monomer, (2) a non-ionic monomer; and (3) a crosslinking monomer.

Exemplary cationic monomers for the crosslinked, cationic polymer may include, for example, acid-neutralized compounds or quaternary ammonium salts of amino group-containing monomers including dialkylamino group-containing (meth)acrylic esters or (meth)acrylamides such as dimethylaminoethyl (meth)acrylate, diethylaminoethyl (meth)acrylate, dipropylaminoethyl (meth)acrylate, diisopropylaminoethyl (meth)acrylate, dibutylaminoethyl (meth)acrylate, diisobutylaminoethyl (meth)acrylate, di-t-butylaminoethyl (meth)acrylate, dimethylaminopropyl (meth)acrylamide, diethylaminopropyl (meth)acrylamide, dipropylaminopropyl (meth)acrylamide, diisopropylaminopropyl (meth)acrylamide, dibutylaminopropyl (meth)acrylamide, diisobutylaminopropyl (meth)acrylamide, and di-t-butylaminopropyl (meth)acrylamide, dialkylamino group-containing styrenes such as dimethylamino styrene and dimethylaminomethyl styrene, vinyl pyridines such as 4-vinyl pyridine and 2-vinyl pyridine, N-vinyl heterocyclic compounds such as N-vinyl imidazole, and vinyl ethers such as aminoethyl vinyl ether and dimethylaminoethyl vinyl ether; and diallyl-having quaternary ammonium salts as dimethyldiallyl ammonium chloride and diethyl diallyl ammonium chloride.

The acids which are advantageously used for producing the acid-neutralized compounds mentioned (for both the ampholytic and crosslinked cationic polymers) include hydrochloric acid, sulfuric acid, nitric acid, acetic acid, formic acid, maleic acid, fumaric acid, citric acid, tartaric acid, adipic acid, sulfamic acid, toluene sulfonic acid, lactic acid, pyrrolidone-2-carboxylic acid, and succinic acid, for example. The quaternizing agents which are advantageously used for producing the quaternary ammonium salts mentioned above include an alkyl halide such as methyl chloride, ethyl chloride, methyl bromide and methyl iodide, and standard alkylating agents such as dimethyl sulfate, diethyl sulfate and di-n-propyl sulfate, for example.

Of these cationic group-containing vinyl monomers, that which proves to be particularly advantageous is at least one member selected from among the compounds represented by the following formula (II) or (III):

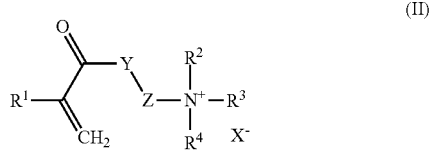

wherein $R^1$ is a hydrogen atom or methyl group, $R^2$ and $R^3$ are identical to or different from each other and each represent an alkyl group or alkenyl group of 1 to 4 carbon atoms, $R^4$ represents a hydrogen atom or an alkyl group of 1 to 4 carbon atoms, Y represents a O, NH, or $OCH_2 CH(OH)$ group, Z represents a linear or branched alkyl and or alkylene group of 1 to 6 carbon atoms and X represents a conjugate base of the acid, a halogen atom, or an alkyl sulfate group of one to four carbon atoms,

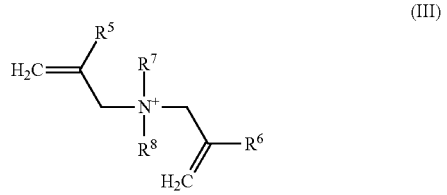

wherein $R^5$ and $R^6$ are identical to or different from each other and each represent a hydrogen atom or a methyl group, $R^7$ and $R^8$ are identical to or different from each other and each represent a hydrogen atom or an alkyl group of one to four atoms, and X represents a conjugate base of the acid, a halogen atom, or an alkyl sulfate group of one to four carbon atoms.

Of the compounds represented by the general formula (II) or (III) mentioned above, those that may be particularly advantageous include the quaternary ammonium salts obtained by quaternizing dimethylaminoethyl (meth)acrylate, diethylaminoethyl (meth)acrylate, dimethylaminopropyl (meth)acrylamide, and diethylaminopropyl (meth)acrylamide with such a quaternizing agent as mentioned below or dimethyldiallyl ammonium chloride, for example.

Exemplary nonionic monomers for the crosslinked, cationic polymer may include, for example, (meth)acrylamide, N-methyl (meth)acrylamide, N,N-dimethyl (meth)acrylamide, N,N-diethyl (meth)acrylamide, N-n-propyl (meth)acrylamide, N-isopropyl (meth)acrylamide, N-t-butyl (meth)acrylamide and N-isobutyl (meth)acrylamide. In a particular embodiment, the nonionic monomer may be a hydrophilic nonionic group-containing vinyl monomer represented by the formula (IV):

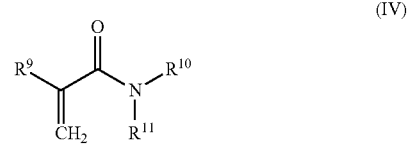

wherein $R^9$ represents a hydrogen atom or methyl group and $R^{10}$ and $R^{11}$ are identical to or different from each other and each represent a hydrogen atom or a linear or branched alkyl group or alkenyl group of 1 to 4 carbon atoms.

Exemplary crosslinking monomers for the crosslinked, cationic polymer may include a cross-linking vinyl monomer containing at least two vinyl groups in the molecular unit thereof, including, (meth)acrylic esters of polyhydric alcohols such as ethylene glycol di(meth)acrylate, diethylene glycol di(meth)acrylate, polyethylene glycol di(meth)acrylate, propylene glycol di(meth)acrylate, dipropylene glycol di(meth)acrylate, polypropylene glycol di(meth)acrylate, 1,2-butylene glycol di(meth)acrylate, 1,3-butylene glycol di(meth)acrylate, neopentyl glycol di(meth)acrylate, glycerin di(meth)acrylate, glycerin tri(meth)acrylate, trimethylolpropane tri(meth)acrylate and pentaerythritol tetra-(meth)acrylate; acryl amides such as N-methylallyl acrylamide, N-vinyl acrylamide, N,N'-methylene bis(meth)acrylamide and bisacrylamide acetic acid; divinyl compounds such as divinyl benzene, divinyl ether and divinyl ethylene urea; polyallyl compounds such as diallyl phthalate, diallyl maleate, diallyl amine, triallyl amine, triallyl ammonium salts, allyl etherified pentaerythritol and allyl etherified sucrose containing at least two allyl ether units in the molecular unit thereof; and (meth)acrylic esters of unsaturated alcohols such as vinyl (meth)acrylate, allyl (meth)acrylate and 2-hydroxy-3-acryloyl oxypropyl (meth)acrylate. In a particular embodiment, ethylene glycol di(meth)acrylate, polyethylene glycol di(meth)acrylate, divinyl benzene, pentaerythritol triallyl ether or pentaerythritol tetraallyl ether may be particularly suitable.

The mixing ratio of the cationic monomer and the hydrophilic nonionic monomer for the production of the crosslinked, cationic polymer of the present disclosure may be in the range of 98/2 to 2/98, preferably in the range of 60/40 to 3/97 inclusive of all ranges, in terms of cationic monomer/hydrophilic nonionic monomer (molar ratio). However, other mixing ratios may be used depending on the desired properties such as thixotropy, etc. Further, the proportion of the cross-linking monomer containing at least two vinyl groups in the molecular unit thereof in the total amount of the component monomers may be in the range of about 0.002 to 5 weight percent (and more particularly in the range of about 0.002 wt. % to 0.1 weight percent).

The crosslinked cationic polymer may be formed by any polymerization technique, such as by aqueous solution polymerization, reversed-phase suspension polymerization, emulsion polymerization, or precipitation polymerization. As the aqueous solution polymerization method, for example, a the polymerization may occur by uniformly dissolving the monomer components and cross-linking agent in water or a hydrophilic organic solvent uniformly mixable with water or a mixed solvent thereof, removing dissolved oxygen from the interior of the reaction system as by displacement with such an inert gas as nitrogen or carbon dioxide gas, and thereafter adding a polymerization initiator, such as those described above with respect to the ampholytic polymer, to the system, thereby inducing the reaction of the monomer components. Depending on the solubility of the monomer components in water, it may be desirable to also use a hydrophilic organic solvent, such as such lower alcohols ($C_1$-$C_3$), cyclic ethers, acetonirtile, dimethyl formamide, dimethyl acetamide and dimethyl sulfoxide, etc.

The compositions of the present disclosure may broadly include at least 0.01 to 10 weight percent of the crosslinked cationic polymer.

In a particular embodiment, the ampholytic polymer is selected from a group of polymers consisting of (1) a polymer comprised of about 40 mol % of methacrylamidopropyl trimethyl ammonium chloride (MAPTAC), about 50 mol % of acrylamide and 10 mol % of acrylic acid and (2) a polymer comprised of about 45 mol % MAPTAC, about 45 mol % acrylic acid, and about 10 mol % methylacrylate, and (3) a polymer comprised of about 30 mol % diallyl dimethyl ammonium chloride (DADMAC), about 35 mol % acrylic acid, and about 35 mol % acrylamide, and (4) a polymer comprised of about 64 mol % DADMAC, about 36 mol % acrylic acid, and where the crosslinked cationic polymer consists of about 1 to 99 wt % N,N-dimethlyaminoethyl methacrylate diethyl sulfate quaternary salt, about 1 to 99 wt % N,N-dimethylacrylamide, and about 0.002-5 wt % polyethylene glycol dimethacrylate copolymer.

In a more particular embodiment, the ampholytic polymer consists of about 40 mol % of MAPTAC, about 50 mol % of acrylamide and 10 mol % of acrylic acid, and the crosslinked cationic polymer comprises about 10 mol % N,N-dimethylaminoethyl methacrylate diethyl sulfate quaternary salt, about 90 mol %, N,N-dimethylacrylamide, about 0.002-5 wt % polyethylene glycol dimethacrylate copolymer.

Carrier

Depending on the end-use of the composition of the present disclosure, the combined polymer components may be incorporated into a carrier including an aqueous and/or organic component.

The compositions of the present disclosure are typically liquids that, in one embodiment, are pourable at room temperature. In certain embodiments, compositions hereof may comprise an aqueous carrier which will generally be present at a level of about 5% to about 95% by weight of the composition, preferably from about 20% to about 95% for pourable, liquid formulations such as shampoos, shower gels, liquid hand-soaps, and lotions. The compositions of the present disclosure may also be in other forms, such as gels, mousse, etc. In such cases, appropriate components known in the art such as gelling agents (e.g., hydroxyethyl cellulose), etc. may be included in the compositions. Gels will typically contain from about 20% to about 99% water. Mousses will be a low viscosity composition and will be packaged as a sprayable liquid according to techniques well known in the art, typically in an aerosol canister including a propellant or a means for generating an aerosol spray.

For example, for skin care formulations, oil in water emulsions will contain amounts, by weight, of the organic liquid of about 3 to about 25%, preferably about 5 to about 20%, with about 6 to 15% being most preferred. Water in oil skin care formulations will contain amounts, by weight, of the organic insoluble liquid of about 25 to about 85%, preferably about 30 to about 60%, with about 35 to about 50% being most preferred.

As used herein, "nonvolatile" refers to a liquid that exhibits very low or no significant vapor pressure at ambient conditions (e.g., 1 atmosphere, 25° C.), as is understood in the art. The nonvolatile oily materials preferably have a boiling point at ambient pressure of about 250° C. or higher.

Further, the organic carrier may be water insoluble. As used herein, "water insoluble" refers to a liquid that is not soluble in water (distilled or equivalent) at a concentration of 0.1%, at 25° C.

Exemplary organic carriers may include liquids selected from the group consisting of hydrocarbon oils. Hydrocarbon oils may include cyclic hydrocarbons, straight chain aliphatic hydrocarbons (saturated or unsaturated), and branched chain aliphatic hydrocarbons (saturated or unsaturated). Straight chain hydrocarbon oils will preferably-contain from about 3 to about 19 carbon atoms, although it is not necessarily meant to be limit the hydrocarbons to this range. Branched chain hydrocarbon oils may and typically will contain higher numbers of carbon atoms. Also encompassed herein are polymeric hydrocarbons of alkenyl monomers, such as $C_2$-$C_6$ alkenyl monomers. These polymers may be straight or branched chain polymers. The straight chain polymers may typically be relatively short in length, having a total number of carbon atoms as described above for straight chain hydrocarbons in general The branched chain polymers may have substantially higher chain length. The number average molecular weight of such materials may vary widely but will typically be up to about 500, preferably from about 50 to about 400, more preferably from about 300 to about 350.

Specific examples of suitable materials include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, may also be used. Exemplary branched-chain isomers are highly branched saturated or unsaturated alkanes, such as the permethyl-substituted isomers (e.g., the permethyl-substituted isomers of hexadecane and undecane, such as 2,2,4,4,6,6,8,8-dimethyl-10-methylundecane and 2,2,4,4,6,6-dimethyl-8-methyinonane). A preferred hydrocarbon polymer is polybutene, such as the copolymer of isobutylene and butene.

The carriers of this disclosure may also include volatile and non-volatile silicone oils or fluids. The silicone compounds may be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane. When used, the silicone oils are preferably included in the formulations of this disclosure at a concentration of 0.1 to 30 weight percent, more preferably 1 to 20 weight percent.

Surfactants

The composition of the present disclosure may include surface-active agents. Surface active agents include surfactants, which typically provide detersive functionality to a formulation or act simply as wetting agents. Surface-active agents may generally be categorized as anionic surface-active agents, cationic surface-active agents, nonionic surface-active agents, amphoteric surface-active agents, and zwitterionic surface-active agents.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used in the compositions of this disclosure are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent (e.g., $SO_3$, $H_2SO_4$, oleum) obtained according to known sulfonation methods, including bleaching and hydrolysis. Preferred are alkali metal and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates, alkyl and acyl glutamates, acyl peptides, and taurates Specific examples of succinamates include disodium N-octadecyl sulfosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid. Exemplary alkyl and acyl glutamates may include mono and dialkyl glutamates, acyl glutamates. Exemplary acyl peptides may include as potassium cocyl hydrolyzed soy protein, potassium cocyl hydrolyzed milk protein, potassium cocyl hydrolyzed collagen, potassium cocyl hydrolyzed rice protein. Exemplary taurates may include sodium lauroyl taurate and sodium methyl cocoyl taurate.

Preferred anionic surface-active agents for use in the cosmetically acceptable composition of this disclosure include ammonium lauryl sulfate, ammonium laureth sulfate, triethylamine laureth sulfate, triethanolamine lauryl sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauryl sarcosinate, lauryl sarcosine, cocoyl sarcosine, ammonium cocoyl sulfate, ammonium lauryl sulfate, sodium cocoyl sulfate, sodium lauryl sulfate, potassium cocoyl sulfate, potassium lauryl sulfate, monoethanolamine cocoyl sulfate, sodium tridecyl benzene sulfonate, and sodium dodecyl benzene sulfonate.

Amphoteric surface-active agents which may be used in the cosmetically acceptable composition of this disclosure include derivatives of aliphatic secondary and tertiary amines, in which the aliphatic substituent contains from about 8 to 18 carbon atoms and an anionic water solubilizing group (e.g., carboxy, sulfonate, sulfate, phosphate, or phosphonate). Representative examples include sodium 3-dodecyl-aminopropionate and sodium 3-dodecylaminopropane sulfonate. Other amphoteric surfactants include n-alkylamino acids like alkylaminopropionic acid, aminopropyl alkylglutamide.

Cationic surface-active agents generally include, but are not limited to fatty quaternary ammonium compounds containing from about 8 to about 18 carbon atoms. The anion of the quaternary ammonium compound may be a common ion such as chloride, ethosulfate, methosulfate, acetate, bromide, lactate, nitrate, phosphate, or tosylate and mixtures thereof. The long chain alkyl groups may include additional or replaced carbon or hydrogen atoms or ether linkages. Other substitutions on the quaternary nitrogen may be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: behentrimonium chloride, cocotrimonium chloride, cethethyldimonium bromide, dibehenyldimonium chloride, dihydrogenated tallow benzylmonium chloride, disoyadimonium chloride, ditallowdimonium chloride, hydroxycetyl hydroxyethyl dimonium chloride, hydroxyethyl behenamidopropyl dimonium chloride, hydroxyethyl cetyldimonium chloride, hydroxyethyl tallowdimonium chloride, myristalkonium chloride, PEG-2 oleamonium chloride, PEG-5 stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, polyquaternium-55, cetyl trimonium chloride, dilauryldimonium chloride, cetalkonium chloride, dicetyldimonium chloride, soyatrimonium chloride, stearyl octyl dimonium methosulfate, and mixtures thereof. Other cationic surfactants may include amines from about $C_{10}$ to $C_{22}$, long chain fatty amines from about $C_{10}$ to $C_{22}$, and mixtures thereof. Specific examples include dipalmitylamine, lauramidopropyldimethyl, stearamidopropyl dimethylamine.

Nonionic surface-active agents, which may be used in the compositions of this disclosure may include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; trimesters of phosphoric acid, like trideceth-3 phosphate, trioleth-8 phosphate, the polyethylene glycol (PEG) glyceryl fatty esters. Other nonionic surfactants include fatty alcohols (typically monohydric alcohols), ethoxylated fatty alcohols, and di-tail phospholipids, which may be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol.

Cetyl alcohol is preferred and may be used alone or in combination with other fatty alcohols, preferably with stearyl alcohol. When used, the fatty alcohol is preferably included in the formulations of this disclosure at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included.

Zwitterionic surface-active agents such as betaines may also be useful in the compositions of this disclosure. Examples of betaines useful herein may include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH(CH$_2$)$_3$ radical is attached to the nitrogen atom of the betaine are also useful in this disclosure. Other surfactants may be found in the CTFA Cosmetic Ingredient Handbook, Twelfth Edition, 2008, incorporated herein by reference.

The anionic, cationic, nonionic, amphoteric or zwitterionic surface-active agents used in compositions of this disclosure may be used in an amount from about 0.1 to 50 percent by weight, preferably from about 0.5 to about 40 percent by weight, more preferably from about 1 to about 20 percent by weight.

The compositions of the present disclosure may be utilized for various consumer and industrial purposes, including personal care products, health care products, household care products, and institutional and industrial products. The term "personal care products" as used herein includes, without limitation, cosmetics, toiletries, cosmeceuticals, beauty aids, personal hygiene and cleansing products that are applied to the skin, hair, scalp, and nails of humans and animals. The term "health care products" as used herein includes, without limitation, pharmaceuticals, pharmacosmetics, cosmeceuticals, oral care products (mouth, teeth), eye care products, ear care products and over-the-counter products and appliances, such as patches, plasters, dressings, and the like. The term also includes medical devices that are externally applied to or into the body of humans and animals for ameliorating a health related or medical condition. The term "body" includes the keratinous (hair, nails) and non-keratinous skin areas of the entire body (face, trunk, limbs, hands and feet), the tissues of body openings and the eyes. The term "skin" includes the scalp and mucous membranes. The term "household care products" as used herein includes, without limitation, products being employed in a household for surface protection and/or cleaning including biocidal cleaning products for maintaining sanitary conditions in the kitchen and bathroom and laundry products for fabric cleaning and the like. The term "institutional and industrial products" as used herein includes, without limitation, products employed for protection and/or cleaning or maintaining sanitary conditions in industrial and institutional environments, including hospitals and health care facilities, and the like.

For example, the compositions may be used for any of shampoos, aftershaves, sunscreens, lotions, hand and body creams, liquid soaps, bar soaps, bath oil bars, shaving creams, dishwashing liquids, detergents, surface cleaners, disposable wipes, conditioners, latex paints, permanent waves, hair relaxers, hair bleaches, hair detangling lotion, hair growth and hair loss preventing products (that contain ingredients like DHT blockers (synthetic or natural) such as minoxidil and saw palmetto extract) styling gel, styling glazes, spray foams, styling creams, styling waxes, styling lotions, mousses, spray gels, pomades, shower gels, bubble baths, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms, insect repellent, bubble generating agent, pet deodorizer or insecticides, pet shampoo agents, industrial grade soap; all-purpose cleaning agents, disinfecting agents, rug and upholstery cleaning actives, laundry softener, laundry detergent, dishwashing detergents, toilet bowl cleaning agents, laundry prespotters, fabric sizing agents, vehicle cleaning agents, textile products such as dusting or disinfecting wipes.

The above list of personal care, health care products, household care products, and institutional and industrial product compositions are only examples and are not a complete list of compositions in which the polymer combination of the present disclosure may be used. Further, depending on the end-use of the composition, other ingredients may be added as appropriate. Other ingredients that are used in these types of products are well known in the industry. In addition to the ingredients conventionally used, the composition according to the present disclosure may optionally also include, but is not limited to, ingredients such as a colorant, preservative, antioxidant, nutritional supplements, alpha or beta hydroxy acid, activity enhancer, emulsifiers, functional polymers, viscosifying agents (water-soluble polymers, e.g., hydroxyethylcellulose, hydroxypropylmethyl cellulose, and fatty alcohols, e.g., cetyl alcohol), alcohols having 1-6 carbons, fats or fatty compounds, antimicrobial compound, zinc pyrithione, silicone materials, hydrocarbon polymer, emollients, oils, surfactants, medicaments, flavors, fragrances, suspending agents, and mixtures thereof.

In particular embodiments, the compositions encompassed by this disclosure may be cosmetically acceptable compositions. In various embodiments, the compositions may contain one or more cosmetically acceptable excipients. In particular embodiments, the cosmetically acceptable excipients may be selected from the group consisting of saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, keratin modifying agents, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylens, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitins, chitins, chitosan, chitosan pyrrolidone carboxylate, chitosan glycolate chitosan lactate, cocodimonium hydroxypropyl oxyethyl cellulose, colominic acid (poly-N acetyl-neuraminic acid), corn starch, curdlan, dermatin sulfate, dextrans, furcellarans, dextrans, crosslinked dextrans, dextrin, emulsan, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, starch hydroxypropyltrimoium chloride, hydroxyproyl starch phosphate, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Examples of microbial saccharides may be found in Kirk-Othmer *Encyclopedia of Chemical Technology*, Fourth Edition, Vol. 16, John Wiley and Sons, NY pp. 578-611 (1994) which is incorporated entirely by reference. Examples of complex carbohydrates may be found in Kirk-Othmer *Encyclopedia of Chemical Technology*, Fourth Edition, Vol. 4, John Wiley and Sons, NY pp. 930-948, 1995 which is herein incorporated by reference.

Monocarboxylic acid esters hereof may include esters of alcohols and/or acids of the formula R' COOR wherein alkyl or alkenyl radicals and the sun of carbon atoms in R' and R is at least 10, preferably at least 20.

Fatty esters may include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples may include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyl decyl adipate, lauryl lactate, myristyl lactate, cetyl lactate, oleyl stearate, oleyl oleate, oleyl myristate, lauryl acetate, cetyl propionate, and oleyl adipate.

The mono-carboxylic acid ester however need not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids may also be used. These include, for example, esters of $C_4$-$C_8$ dicarboxylic acids such as $C_1$-$C_{22}$ esters (preferably $C_1$-$C_6$) of succinic acid, glutaric acid, adipic acid, hexanoic acid, heptanoic acid, and octanoic acid. Specific examples may include isocetyl stearyl stearate, diisopropyl adipate, and tristearyl citrate. Polyhydric alcohol esters include alkylene glycol esters, for and di-fatty acid esters, diethylene example ethylene glycol mono glycol mono- and di-fatty acid esters, polyethylene glycol mono and di-fatty acid esters, propylene glycol mono- and di-fatty acid esters, polypropylene glycol mono oleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters are satisfactory polyhydric alcohol esters for use herein.

Glycerides may include mono-, di-, and tri-glycerides. More specifically, included are the mono-, di-, and tri-esters of glycerol and long chain carboxylic acids, such as $C_{10}$-$C_{22}$ carboxylic acids. A variety of these types of materials may be obtained from vegetable and animal fats and oils, such as castor oil, safflower oil, cotton seed oil, corn oil, olive oil, cod liver oil, almond oil, avocado oil, palm oil, sesame oil, lanolin and soybean Synthetic oils may include triolein and tristearin glyceryl dilaurate. Preferred glycerides are di-, and tri-glycerides. Especially preferred are triglycerides.

A cosmetically acceptable composition of this disclosure may include humectants, which act as hygroscopic agents, increasing the amount of water absorbed, held and retained. Suitable humectants for the formulations of this disclosure include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

A cosmetically acceptable composition of this disclosure may include petrolatum or mineral oil components, which when selected will generally be USP or NF grade. The petrolatum may be white or yellow. The viscosity or consistency grade of petrolatum is not narrowly critical. Petrolatum may be partially replaced with mixtures of hydrocarbon materials, which may be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, sythetic beeswax and the like may be blended together. Alkylmethyl siloxanes with varying degrees of substitution may be used to increase water retained by the skin. Siloxanes such as stearyl dimethicone, $C_{30}$-$C_{45}$ alkyl methicone, and stearoxytrimethylsilane (and) stearyl alcohol. Additional alkyl and phenyl silicones may be employed to enhance moisturizing properties. Resins such as dimethicone (and) trimethylsiloxysilicate, or cyclomethicone (and) trimethylsiloxysilicate, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins may be included from about 0.1 to about 10.0 weight percent.

Silicone surfactants or emulsifiers with polyoxyethylene or polyoxypropylene side chains may also be used in compositions of the current invention. The side chains may also include alkyl groups such as lauryl or cetyl. Preferred are lauryl methicone copolyol and cetyl dimethicone copolyol. When used, the silicone surfactants are preferably included in the formulations of this invention at a concentration of 0.1 to 30 weight percent, more preferably 1 to 15 weight percent.

Amine functional silicones and emulsions may be utilized in the present invention. When used, the amine functional silicones are preferably included in the formulations of this invention at a concentration of 0.1 to 5 weight percent, more preferably 0.1 to 2.0 weight percent.

Emollients are defined as agents that help maintain the soft, smooth, and pliable appearance of skin. Emollients function by their ability to remain on the skin surface or in the stratum corneum. A cosmetically acceptable composition of this disclosure may include fatty ester emollients, which are listed in the International Cosmetic Ingredient Dictionary, Eighth Edition, 2000, p. 1768 to 1773. Specific examples of suitable fatty esters for use in the formulation of this disclosure include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this disclosure at a concentration of about 1 to about 8 weight percent, more preferably about 2 to about 5 weight percent.

The compositions of this disclosure may also include silicone compounds. Preferably, the viscosity of the silicone component at a temperature of 25° C. is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane endblocked with trimethyl units, is one preferred example. Dimethicone having a viscosity between 50 and 1,000 cps is particularly preferred. When used, the silicone oils are preferably included in the formulations of this disclosure at a concentration of 0.1 to 5 weight percent, more preferably 1 to 2 weight percent.

Compositions of this disclosure may include volatile and non-volatile silicone oils or fluids. The silicone compounds may be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane. When used, the silicone oils are preferably included in the formulations of this disclosure at a concentration of 0.1 to 30 weight percent, more preferably 1 to 20 weight percent.

Cosmetically acceptable compositions of this disclosure may include volatile, cyclic, low molecular weight polydimethylsiloxanes (cyclomethicones). The examples of cyclic polydimethylsiloxanes may be polydimethyl cyclosiloxanes having an average repeat unit of 4 to 6, and a viscosity from about 2.0 to about 7.0 centistokes, and mixtures thereof. When used, the silicone oils are preferably included in the formulations of this disclosure at a concentration of 0.1 to 30 weight percent, more preferably 1 to 20 weight percent.

Silicone surfactants or emulsifiers with polyoxyethylene or polyoxypropylene side chains may also be used in compositions of the current disclosure. The side chains may also include alkyl groups such as lauryl or cetyl. Preferred are lauryl methicone copolyol and cetyl dimethicone copolyol. When used, the silicone surfactants are preferably included in the formulations of this disclosure at a concentration of 0.1 to 30 weight percent, more preferably 1 to 15 weight percent.

Amine functional silicones and emulsions may be utilized in the composition of the present disclosure. When used, the amine functional silicones are preferably included in the formulations of this disclosure at a concentration of 0.1 to 5 weight percent, more preferably 0.1 to 2.0 weight percent.

The compositions of this disclosure may also include volatile hydrocarbon oils. The volatile hydrocarbon comprises about $C_6$ to $C_{22}$ atoms. A preferred volatile hydrocarbon is an aliphatic hydrocarbon having a chain length of about $C_6$ to $C_{16}$ carbon atoms. An example of such compound includes isohexadecane. Another example of a preferred volatile hydrocarbon is $C_{12}$ to $C_{14}$ isoparaffin. When used, the volatile hydrocarbons are preferably included in the formulations of this disclosure at a concentration of 0.1 to 30 weight percent, more preferably 1 to 20 weight percent.

The compositions of this disclosure may also include other cationic and ampholytic conditioning polymers. Examples of such include, but are not limited to those listed by the International Cosmetic Ingredient Dictionary published by the Cosmetic, Toiletry, and Fragrance Association (CTFA) Twelfth Edition 2008. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-24, Polyquaternium-28, Polyquaternium-32, Polyquaternium-33, Polyquaternium-36, Polyquaternium-37, Polyquaternium-45, and polymethacrylamidopropyltrimonium chloride, Polyquaternium-55 and mixtures thereof. When used, the conditioning polymers are preferably included in the cosmetically acceptable composition of this disclosure at a concentration of from 0.1 to 10 weight percent, preferably from 0.2 to 6 weight percent and most preferably from 0.2 to 5 weight percent.

The compositions of this disclosure may be prepared as an aqueous product, oil-in-water, water-in-oil emulsions, multiple emulsions, or dispersions.

Preferred oil-in-water emulsions are prepared by first forming an aqueous mixture of the water-soluble components (e.g. quaternary ammonium compounds, the humectant, water-soluble preservatives) followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

The composition of this disclosure may also be packaged as an aerosol, in which case it may be applied either in the form of an aerosol spray or in the form of an aerosol foam. As the propellant gas for these aerosols, it is possible to use both exempt and non-exempt volatile organic compounds in particular, dimethyl ether, carbon dioxide, nitrogen, nitrous oxide, air and volatile hydrocarbons, such as butane, isobutane, and propane.

Compositions for treating hair include bath preparations such as bubble baths, soaps, and oils, shampoos, conditioners, hair bleaches, hair coloring preparations, temporary and permanent hair colors, hair conditioners, hair lighteners, coloring and non-coloring hair rinses, hair tints, hair wave sets, permanent waves, curling, hair straighteners, hair grooming aids, hair tonics, hair dressings and oxidative products, hair growth and hair loss preventing products containing ingredients like DHT blockers (both synthetic and natural), styling type leave-in products such as gels, mousses, spritzes, styling creams, styling waxes, pomades, balms, and the like, either alone or in combination with other polymers or structuring In a particular embodiment, the polymer combination of the present disclosure may be particularly suitable for hair care compositions, such as shampoos, including shampoos for dyed hair. Specifically, the use of the combination of the polymers of the present disclosure in hair care compositions of this disclosure may give a slippery feel and be easily rinsed from the hair, offer good foaming characteristics, and provide excellent color retention due to the presence of the both the ampholytic polymer and the crosslinked cationic polymer (and their synergistic effect), other polymers, surfactants or other compounds that may alter the deposition of materials upon the hair. The combination of both ampholytic polymer and the crosslinked cationic polymer may also provide smooth feel, conditioning property both in wet and dry state, similar to silicone, may also provide static reduction (non-fly away hair), hair damage prevention, improvement of hair elasticity and strength.

In the case of cleansing formulations such as a shampoo for washing the hair, or a liquid hand soap, or shower gel for washing the skin, the compositions may contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos of this disclosure may contain combinations of anionic surfactants with zwitterionic surfactants and/or amphoteric surfactants. However, in a particular embodiment, the foaming characteristics of the combined ampholytic polymer and crosslinked cationic polymer of the present disclosure may allow for the avoidance (or minimization) of the use of known high sudsing anionic surfactants with foam boosters that provide acceptable lather volume but that also give a high skin irritation. While mild surfactants give minimal skin irritation, they may be extremely poor in lather. Thus, because the combination of the polymers of the present disclosure provide good foam/lather characteristics, the selection of the surfactants may be less dependent on the necessity of lather, and a more mild surfactant may be more freely used, particularly in compositions in contact with skin.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they may be water in oil or oil in water or multiple emulsions containing nonionic, anionic or cationic surfactants.

If the compositions are presented in the form of a thickened lotion or a gel, they contain thickeners. The thickeners which may be used are especially resins, acrylic acid thickeners; xanthan gums; sodium alginates; gum arabic; cellulose derivatives and poly(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight.

If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of from about 0.25 to about 10 percent by weight. The additional hair fixative resin may be selected from the following group as long as it is compatible with a given polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyquaternium-55, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylates copolymer, sodium acrylates/Acrylnitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, polyacrylate 21 and acrylates/dimethylaminoethyl methacrylate copolymer, and mixtures thereof. Examples of synthetic polymers used for creating styling aids are described in "The History of Polymers in Haircare," Cosmetics and Toiletries, 103 (1988), incorporated herein by reference. Other synthetic polymers that may be used with the present disclosure may be referenced in the CTFA Dictionary, Twelfth Edition, 2008, incorporated herein by reference.

If the compositions of the instant disclosure are intended for use in the dyeing of keratin fibers, and in particular human hair, they generally contain at least one oxidation dyestuff precursor, a coupler and/or one direct dyestuff, in addition to the ampholytic polymer and crosslinked cationic polymer. They may also contain any other adjuvant normally used in this type of composition.

Further, while specific embodiments of cosmetically acceptable compositions have been given, the compositions encompassed by this disclosure may be applied to various types of substrates, as mentioned above, a household surface or an industrial surface. For example, the substrate on which the compositions of the present disclosure are applied may be selected from hair, skin, nails, a keratin containing substrate, a hard surface, a carpet, a fabric, wood, a plastic containing composition, or vinyl, for example.

EXAMPLES

The following examples are provided to demonstrate the synergistic effect on properties for a composition of the present disclosure. The following examples are intended for illustrative purposes and are not intended to limit the scope of the invention.

Example 1

A hair color retention test was conducted on virgin level 12 white hair tresses purchased from International Hair Importers (Glendale, N.Y.). Two hair tresses, weighing 2 g each were treated with 8 g of L'OREAL® permanent color R68 mixed with 20V developer for 25 minutes. The swatches were rinsed with water running at a rate of 3.8 lit/min for 1 minute. The hair swatches were then shampooed with 3% ALS solution by applying 1 g of ALS solution for 30 sec, hold for 1 minute, and rinsed with tap water at a rate of 3.8 lit/min for 1 min and later with deionized water for 15 sec. The swatches were allowed to dry overnight in a humidity room at a relative humidity of 65%. The next day the swatches were shampooed again with 3% ALS by following the procedure given above and kept in the humidity room overnight. The following day the tresses were shampooed with the following shampoos the composition shown in Table 1 below. Shampoo A includes MERQUAT® 5210, a crosslinked cationic polymer, available from Nalco Company (Naperville, Ill.; a preservative free formulation made up of N,N-dimethylaminoethyl methacrylate ethyl sulfate quaternary salt (DMAEM-ESQ), dimethyl acrylamide (DMAA) and PEG-dimethacrylate) and MERQUAT® 2003PR, an ampholytic polymer, also available from Nalco Company (an amphoteric linear terpolymer, made up of acrylic acid, MAPTAC and acrylamide, supplied as a 20% solution in water) at a concentration of 0.1 and 0.2%, respectively. Shampoo B includes 0.1% MERQUAT® 5210, Shampoo C contains 0.2% MERQUAT® 2003PR, and Shampoo D is the control and includes neither polymer.

TABLE 1

| | A | B | C | D |
|---|---|---|---|---|
| Deionized Water | 45.03 | 46.03 | 55.73 | 56.30 |
| Sodium Benzoate | 0.30 | 0.30 | 0.30 | 0.30 |
| Sodium Laureth Sulfate (25%) | 6.80 | 6.80 | 6.80 | 6.80 |
| Cocamidopropyl Betaine (30%) | 35.00 | 35.00 | 35.00 | 35.00 |
| MERQUAT® 5210 (40%) | 0.27 | 0.27 | 0.00 | 0.00 |
| MERQUAT® 2003PR (20%) | 1.00 | 0.00 | 1.00 | 0.00 |
| NaCl Solution (20%) | 1.50 | 1.50 | 1.50 | 1.50 |
| Citric Acid (50%) | 0.10 | 0.10 | 0.10 | 0.10 |

Each swatch was treated with 1 g of shampoo for 30 sec by messaging between the palms and hold for 1 min and rinsed for 1 min by following the procedure mentioned above. The swatches were gently blotted and allowed to dry at room temperature for 4 h. After 4 h, the initial L, a, b color measurements were recorded using Hunter Colorimeter as base values. The swatches were shampooed a total of 20 times and readings were taken at an interval of 5, 10, 15 and 20 washes. The Hunter Tristimulus L, a, b values were measured using a Hunter Colorimeter LabScan XE (Hunter Associates, Reston, Va.). The data was expressed as total color change $\Delta E=[\Delta L^2+\Delta a^2+\Delta b^2]^{1/2}$ before and after washings. The $\Delta E$ values are the average of measurements performed at several positions, and are shown in Table 2 below. The lower $\Delta E$ value the less color fading before and after washings, which is desirable for these compositions.

| | Delta E | | | |
|---|---|---|---|---|
| Name | 5 Times | 10 Times | 15 Times | 20 Times |
| Composition A | 0.5 | 0.7 | 0.4 | 0.6 |
| Composition B | 2.0 | 3.4 | 3.8 | 4.5 |
| Composition C | 1.4 | 1.3 | 1.3 | 2.5 |
| Composition D (Control) | 1.3 | 3.0 | 3.9 | 4.2 |

The results show the lowest Delta E value for a combination of MERQUAT® 5210 and MERQUAT® 2003PR combination, significant at 95% confidence. The unexpectedly lowest Delta E value for composition A demonstrates that there is a synergistic effect between the two polymers to help in protecting hair color fading from shampooing.

Example 2

The compositions from Example 1 were then subjected to a foam test (Hart DeGeorge). The foam test measures the amount of time taken by foam generated from a shampoo to pass through a 20 mesh sieve. About 200 g of the shampoo solution, 10% by weight in deionized water, is mixed in a commercial blender at a high speed for 60 seconds. The gauging wire is placed near the bottom of the funnel. The time for the level of foam to reach the wire is recorded. A higher retention time is preferred. Each sample is then poured into a funnel having a gauging wire placed near the bottom and the time taken by the foam to reach the wire is recorded. If the foam generated has a large bubble or has low density it takes a lower time to travel compared to foam which has a small bubble size and a high density.

The Hart DeGeorge foam results are shown in Table 3 below. The results show retention time in seconds. The results show that Shampoo containing both MERQUAT® 5210 and MERQUAT® 2003PR (Shampoo A) at a concentration of 0.1 and 0.2%, respectively, generates the best foam. It had the longest retention time of 56 seconds, this was an unexpected value and was significantly high compared to the rest, particularly the control. The results show a synergy between the two polymers as individual polymers showed a lower retention time than the combination. Additionally, the foam generated by this combination had a small bubble size, it was very dense, creamy and had a cushiony feel, an attribute preferred by consumers.

TABLE 3

| Treatment | Run 1 | Run 2 | Run 3 | Average | Std Dev |
|---|---|---|---|---|---|
| Composition A | 54 | 58 | 56 | 56 | 2 |
| Composition B | 24 | 23 | 25 | 24 | 1 |
| Composition C | 35 | 35 | 36 | 35 | 0.57735 |
| Composition D | 8 | 8 | x | 8 | 0 |

Embodiments of the present disclosure may provide at least one of the following advantages. The compositions may provide excellent cleaning, conditioning, as well as color retention, properties for use in a wide variety of personal, household, and industrial products. Specifically, improved overall conditioning, with good foam and color retention properties may be synergistically achieved by combining the ampholytic polymer and crosslinked cationic polymer of the present disclosure. These compositions may provide improved conditioning, lather, and color protection while reducing the level of undesirable side effects that can result from increasing the level of conditioning agent in prior known conditioning systems. The combination of these two components may provide a synergistic effect, whereby the improvement in properties achieved when the two polymer components are used together is significantly improved over use of the two polymer components independently. When used in hair care products, the compositions of the present disclosure may give a slippery feel and be easily rinsed from the hair, offer good foaming characteristics, and provide excellent color retention due to the presence of the both the ampholytic polymer and the crosslinked cationic polymer (and their synergistic effect), other polymers, surfactants or other compounds that may alter the deposition of materials upon the hair. The combination of both ampholytic polymer and the crosslinked cationic polymer may also provide smooth feel, conditioning property both in wet and dry state, similar to silicone, may also provide static reduction (non-fly away hair), hair damage prevention, improvement of hair elasticity and strength.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The invention claimed is:

1. A cleansing composition for cosmetic or household use, comprising:
about 0.2 wt. % of an ampholytic polymer comprising about 40 mol % of methacrylamidopropyl trimethyl ammonium chloride (MAPTAC), about 50 mol % of acrylamide and 10 mol % of acrylic acid;
about 0.1 wt. % of a crosslinked cationic polymer comprising about 10 mol % N,N-dimethylaminoethyl methacrylate diethyl sulfate quaternary salt, about 90 mol % N,N-dimethylacrylamide, and about 0.002-5 wt % polyethylene glycol dimethacrylate copolymer;
a surfactant component selected from the group consisting of anionic surfactants, amphoteric surfactants, cationic surfactants, nonionic surfactants, and zwitterionic surfactants; and
an aqueous and/or organic carrier.

2. The composition of claim 1, wherein said anionic surfactant is selected from the group consisting of lauryl sulfate, lauryl ether sulfate, α-olefin sulfonates, and their ammonium, sodium and amine salts; said nonionic surfactant is selected from the group consisting of fatty di or mono ethanol amides, mono or di fatty esters of polyethylene or polypropylene glycol, and mono or di fatty esters of $C_1$-$C_6$ glycols; said zwitterionic surfactants are selected from the group consisting of alkyl betaines and sulfobetaines.

3. A method of treating a surface comprising applying the composition of claim 1 to a household surface, an industrial surface, a hard surface, a carpet, a fabric, wood, vinyl or a plastic containing composition.

4. A method of treating a surface comprising applying the composition of claim 1 to hair, skin, nails, or a keratin containing substrate.

5. A method for treating keratin substrate comprising contacting hair with the composition of claim 1.

* * * * *